US012740831B2

(12) United States Patent
Wang et al.

(10) Patent No.: US 12,740,831 B2
(45) Date of Patent: Sep. 22, 2026

(54) INTELLIGENT ANESTHETIZATION SYSTEM FOR TRANSPERINEAL PROSTATE PUNCTURING BASED ON MULTIMODAL MEDICAL IMAGES

(71) Applicant: Carbon (Shenzhen) Medical Device Co, Ltd., Shenzhen (CN)

(72) Inventors: Shanshan Wang, Shenzhen (CN); Xiaowei Yang, Shenzhen (CN); Mengling Wu, Shenzhen (CN)

(73) Assignee: Carbon (Shenzhen) Medical Device Co, Ltd., Shenzhen (CN)

( * ) Notice: Subject to any disclaimer, the term of this patent is extended or adjusted under 35 U.S.C. 154(b) by 168 days.

(21) Appl. No.: 18/769,427

(22) Filed: Jul. 11, 2024

(65) Prior Publication Data

US 2025/0017659 A1 Jan. 16, 2025

(30) Foreign Application Priority Data

Jul. 13, 2023 (CN) ......................... 202310857773.0

(51) Int. Cl.
*A61B 34/10* (2016.01)
*A61B 10/02* (2006.01)
(Continued)

(52) U.S. Cl.
CPC .......... *A61B 34/10* (2016.02); *A61B 10/0233* (2013.01); *A61B 17/34* (2013.01);
(Continued)

(58) Field of Classification Search
CPC ..... A61B 34/10; A61B 10/0233; A61B 17/34; A61B 2034/105; A61B 2034/107; A61B 2034/108; A61B 2090/364; A61B 2090/378; G06T 7/12; G06T 7/168; G06T 7/174; G06T 7/38; G06T 19/003;
(Continued)

(56) References Cited

U.S. PATENT DOCUMENTS

2013/0338477 A1* 12/2013 Glossop ............ A61B 10/0241 600/407
2022/0001207 A1* 1/2022 Piper ......................... A61F 7/00
2023/0100078 A1* 3/2023 Toporek ............... A61B 6/5247 382/131

FOREIGN PATENT DOCUMENTS

CN 112971982 A * 6/2021 ............... G06T 5/50
WO WO-2018183217 A1 * 10/2018 ............ A61N 7/022

* cited by examiner

*Primary Examiner* — Kaitlyn E Sebastian
(74) *Attorney, Agent, or Firm* — Bayramoglu Law Offices LLC

(57) ABSTRACT

An intelligent anesthetization system for transperineal prostate puncturing based on multimodal medical images is provided. The system includes a coordinate system definition module, a markup of MRI sequence image and 3D reconstruction module, an ultrasonic data extraction module, a registration module and an anesthetic planning module. This system transforms images in the preoperative nuclear magnetic imaging coordinate system as well as the target area of anesthetization into real-time electromagnetic emitter coordinate system through multimodal medical image registration, thereby realizing the comprehensive fusion of the target area of anesthetization in nuclear magnetic resonance image and ultrasonic image, which can be used for medical teaching or surgical guidance and can help to achieve precise positioning of anesthetized area for transperineal prostate biopsy.

9 Claims, 5 Drawing Sheets

(51) Int. Cl.
*A61B 17/34* (2006.01)
*G06T 7/12* (2017.01)
*G06T 7/168* (2017.01)
*G06T 7/174* (2017.01)
*G06T 7/38* (2017.01)
*G06T 19/00* (2011.01)

(52) U.S. Cl.
CPC ................ *G06T 7/12* (2017.01); *G06T 7/168* (2017.01); *G06T 7/174* (2017.01); *G06T 7/38* (2017.01); *G06T 19/003* (2013.01); *A61B 2034/105* (2016.02); *A61B 2034/107* (2016.02); *A61B 2034/108* (2016.02); *G06T 2207/10028* (2013.01); *G06T 2207/10088* (2013.01); *G06T 2207/10132* (2013.01); *G06T 2207/20084* (2013.01); *G06T 2207/20221* (2013.01); *G06T 2207/30081* (2013.01)

(58) Field of Classification Search
CPC . G06T 2207/10028; G06T 2207/10088; G06T 2207/10132; G06T 2207/20084; G06T 2207/20221; G06T 2207/30081; G06T 5/50; G06T 7/33; G06T 17/00; G06T 7/11; G06T 2210/41; G06T 7/30; G06T 7/70; G06T 2207/20081; G06V 10/26; G06V 10/774; G06V 2201/031; G06V 10/267; G06V 10/82; G16H 30/40; G16H 20/17; G16H 20/40; Y02A 90/30
See application file for complete search history.

z
Nuclear Magnetic Imaging
Coordinate System
x
y z
x
Sensor Coordinate
System
y

Electromagnetic Emitter
Coordinate System
z
y
x

Registration

Navigation

According to collected perineal surface points, the puncture starting plane is fitted.

INTELLIGENT ANESTHETIZATION SYSTEM FOR TRANSPERINEAL PROSTATE PUNCTURING BASED ON MULTIMODAL MEDICAL IMAGES

CROSS REFERENCE TO THE RELATED APPLICATIONS

This application is based upon and claims priority to Chinese Patent Application No. 202310857773.0, filed on Jul. 13, 2023, the entire contents of which are incorporated herein by reference.

TECHNICAL FIELD

The present invention relates to technical field of image processing, and in particular to an intelligent anesthetization system for ultrasonic transperineal puncturing biopsy of prostate based on multimodal medical image registration.

BACKGROUND

With the development of science and technology and the popularization of health education, men around the world are paying more and more attention to prostate diseases. Prostate cancer is also the second most common cancer among men in the world which seriously affects men's health. Doctors usually test prostate-specific antigen (PSA), perform multi-parameter magnetic resonance imaging on patients with abnormal PSA levels, and arrange puncturing biopsy to effectively screen for prostate cancer at an early stage and formulate a treatment plan in a timely manner.

Therefore, how to efficiently complete puncturing biopsy and how to improve positive rate of biopsy results has become a goal that medical community continues to pursue. There are two main types of procedure in prostate biopsy:

The first type is the transrectal puncturing method that has been used for years. This method does not have high requirements for anesthetization and is easy to operate. However, a disadvantage is that rectal bacteria can easily enter the blood causing fever and infection and even the possibility of sepsis. According to statistics, the infection rate of this method is as high as 5-7%;

The second type is transperineal puncturing method which has been widely used in recent years and is relatively safer. According to statistics, the infection rate is compared with transrectal puncturing reduced to 0.075%. Generally, it can be cured in a short time. However, the method has high requirements for anesthetization. People not only need to accurately find anesthetized area, but also need to choose an anesthetic needle with corresponding length for precise anesthetization. If the anesthetic effect is not ideal, the patient can feel very painful during puncturing process, and it may even lead to the inability to successfully complete the surgery. It is precisely because of this reason that large-scale promotion of this safe as well as effective procedure has encountered certain resistance.

Multi-parameter magnetic resonance imaging (mpMRI) is used as the image that must be obtained before prostate puncturing due to its excellent visualization effect on soft tissue. The area of suspected lesions can be identified with relative accuracy on nuclear magnetic resonance image (MRI), and nerve anesthetized area around prostate can also be accurately identified. Ultrasound imaging has a high degree of real-time characteristics and is usually used as preferred equipment for puncturing. However, due to its low quality in image resolution, it is often relatively difficult to identify the precise target area of anesthetization directly on ultrasonic images.

Therefore, there is urgent need for a system that can project anesthetized area in magnetic resonance imaging into real-time ultrasonic images accurately and in real time.

SUMMARY

Purpose of the present invention is to propose an intelligent anesthetization system for the ultrasonic transperineal prostate puncturing based on multimodal medical images in response to current difficulty in identifying precise target area of anesthetization directly on ultrasonic images. The system is simple to operate which uses ultrasonic images to fuse preoperative multi-parameter magnetic resonance images. It accurately integrates anesthetized area and perineum area into high real-time ultrasonic images. At the same time, it intelligently recommends anesthetic tools to achieve accurate preoperative anesthetic plans, thereby not only difficulty of transperineal puncturing but also patient's infection rate can be effectively reduced. The technical solution of the present invention is:

An intelligent anesthetization system for the transperineal prostate puncturing based on multimodal medical images, characterized in that the system comprises:

Coordinate system definition module: Define electromagnetic emitter coordinate system CSe based on the ultrasonic imaging plane formed by the electromagnetic field transmitter, define nuclear magnetic imaging coordinate system CSm based on the nuclear magnetic device for taking MRI sequence images and define coordinate system CSs based on electromagnetic sensor which is fixed on ultrasonic probe; obtain transformation matrix TMse of electromagnetic sensor at any position in CSs based on the position and posture of electromagnetic sensor in the electromagnetic emitter coordinate system CSe;

Markup of MRI sequence image and 3D reconstruction module: Receive MRI sequence images of human prostate, mark anesthetized area MRI-VMa and outer contour area of the prostate MRI-VMp; reconstruct 3D anesthetized area and 3D outer contour area of prostate based on the position information of MRI sequence images;

Ultrasonic data extraction module: Receive ultrasonic data of the human prostate, extract image set covering base to apex of prostate in ultrasonic data, and obtain the outer contour area of prostate US-VMp in the electromagnetic emitter coordinate system CSe under ultrasonic images based on the spatial position information of each frame of ultrasonic image;

Registration module: Use iterative closest point (ICP) point cloud registration algorithm to register volume data about the outer contour area of prostate MRI-VMp in nuclear magnetic imaging coordinate system CSm as well as volume data about the outer contour area of prostate US-VMp in electromagnetic emitter coordinate system CSe under ultrasonic image and obtain the spatial transformation matrix TMme between the two;

Anesthetic planning module: Receive the current ultrasonic image acquired by ultrasonic probe, obtain anesthetized area EMTS-Vma mapped in electromagnetic emitter coordinate system based on spatial transformation matrix TMme, and fuse it with current ultrasonic image to obtain the anesthetized area under ultrasonic images.

Furthermore, the markup specifically uses a pre-trained deep learning model for prostate segmentation to segment MRI sequence images and marks the segmented anesthetized area VMa and the outer contour area of prostate VMp.

Furthermore, the deep learning model for prostate segmentation is specifically established as follows:

Extract the cross-sectional and sagittal images of MRI sequence images of the prostate;

Mark and segments the anesthetized area and the outer contour area of prostate on cross-sectional and sagittal images;

Input marked and segmented MRI images of the prostate as samples into artificial neural network model for training to obtain the deep learning model for prostate segmentation.

Furthermore, the transformation matrix TMse is specifically:

$$TMse = \begin{bmatrix} R & T \\ 0 & 1 \end{bmatrix}$$

Wherein: R is a 3×3 matrix, T is a 3×1 vector, R and T represent the position and posture of electromagnetic sensor in the electromagnetic emitter coordinate system CSe.

Furthermore, the acquisition of outer contour area of prostate US-VMp is specifically:

Extract the image set covering base to apex of the prostate in ultrasonic data, and the frame number is recorded as N;

Extract images containing prostatic organ and segment the outer contour area of prostate to obtain outer contour area of the prostate US-VMp in ultrasonic images, and obtain coordinate PCe of each point within outer contour area in electromagnetic emitter coordinate system CSe using the following formula:

$$PCe_{(i,u,v)} = TMsei \times TMts \times (u, v, 0, 1);$$

Wherein i represents frame number, (u, v) represents pixel coordinates of contour point in ultrasonic 2D images, TMsei represents transformation matrix of electromagnetic sensor at any position in CSs corresponding to i-th frame image, and TMts represents transformation matrix of the relative positions between vertices of ultrasonic imaging plane and electromagnetic sensor.

Furthermore, the registration is specifically:

Use coordinates $PCe_{(i,u,v)}$ of each point in the outer contour area of prostate US-VMp within ultrasonic image in electromagnetic emitter coordinate system CSe as first set of 3D point clouds and use 3D point cloud corresponding to the 3D outer contour area of prostate MRI-VMp as the second set of 3D point clouds;

Process two sets of point clouds separately;

Register the processed 3D point clouds using ICP point cloud registration algorithm to obtain spatial transformation matrix TMme from the nuclear magnetic imaging coordinate system CSm to the electromagnetic emitter coordinate system CSe.

Furthermore, the anesthetic planning module performs the following steps:

Transform anesthetized area MRI-VMa in nuclear magnetic imaging coordinate system CSm into the electromagnetic emitter coordinate system under current ultrasonic images based on spatial transformation matrix TMme to obtain the mapped anesthetized area EMTS-Vma;

Obtain a slice formed by tangency of plane position of current ultrasonic image and of volume data of anesthetized area EMTS-Vma to obtain slice Sa with outline of anesthetized area;

Fuse and superimpose current ultrasonic image and slice Sa with outline of anesthetized area to obtain a fused image of current ultrasonic image and anesthetized area which displays the anesthetized area under the ultrasonic images.

Furthermore, the system which includes a puncture planning module as well performs the following steps:

Extract point cloud data of perineum in electromagnetic emitter coordinate system CSe from ultrasonic data and fits plane position of perineum PP as the initial plane position of the needle into human body, which its normal vector of this plane is consistent with the direction of the ultrasonic probe entering the human body;

Calculate the distance from center point of mapped anesthetized area EMTS-Vma under ultrasonic image to puncture starting plane PP, and recommend the anesthetic needle with suitable length based on distance from anesthetized area to puncture starting plane.

Furthermore, the fitting of plane position PP of perineum comprises:

Extract the ultrasonic data sequence of perineum, and obtain a series of coordinate points PPi(x, y, z, 1) on ultrasonic imaging plane wherein i represents serial number of coordinate points, x, y, z represent coordinate values of ultrasonic imaging plane respectively, and use the following formula to obtain real coordinates PPsi of each point in electromagnetic emitter coordinate system CSs;

$$PPsi = TMse \times TMts \times PPi$$

Wherein: TMts represents transformation matrix of relative positions between vertices of ultrasonic imaging plane and electromagnetic sensor;

Fit plane position PP of perineum as puncture starting plane by the singular value decomposition (SVD) method based on discrete points according to real coordinates PPsi of each point;

$$ax + by + cz + d = 0.$$

Furthermore, the distance from center point of mapped anesthetized area EMTS-Vma to puncture the starting plane PP is calculated using the following formula:

$$d = |ax_m + by_m + cz_m + d| / (a^2 + b^2 + c^2)$$

Wherein $(x_m, y_m, z_m)$ is the center point of the anesthetized area in electromagnetic emitter coordinate system CSe of ultrasonic imaging plane, and a, b, c, d are plane parameters of PP.

The beneficial effects of the present invention are as follows:

The system of present invention transforms the images in preoperative nuclear magnetic imaging coordinate system and target area of anesthetization into real-time electromagnetic emitter coordinate system via multimodal medical image registration, thereby realizing the comprehensive fusion of target area of anesthetization in nuclear magnetic resonance imaging and ultrasonic image which can be used for medical teaching or surgical guidance and can help to achieve the precise positioning of anesthetized area for the transperineal prostate biopsy.

The present invention realizes intelligent recommendation of model of anesthetic needle by calculating and analyzing distance between target area and starting position of needle insertion, making the working progress of anesthetization more smoothly as well as efficiently and playing effective role in promoting procedure in transperineal prostate biopsy.

Other features and advantages of present invention will become apparent from following detailed description of the embodiments of the invention.

BRIEF DESCRIPTION OF THE DRAWINGS

The above and other objects, features and advantages of present invention will be better understood from following detailed description taken in conjunction with accompanying drawings, wherein like reference numerals generally represent like parts in the exemplary embodiment of the present invention.

DETAILED DESCRIPTION OF THE EMBODIMENTS

The present invention will be described more fully hereinafter with the reference to the accompanying drawings, in which a preferred embodiment of invention is shown. This invention may, however, be embodied in many different forms and should not be limited to the embodiments set forth herein.

Embodiment 1

Figure 4:
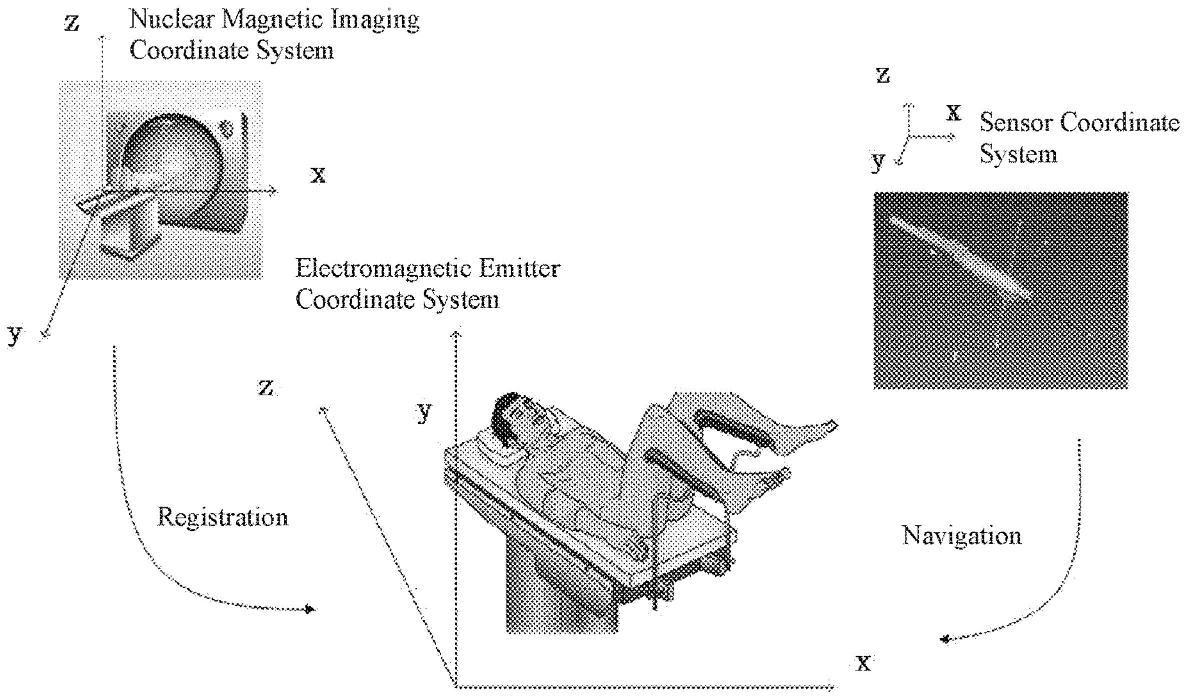
FIG. 4 is a schematic diagram showing the different coordinate systems in the process of anesthetization navigation according to an embodiment of the present invention.
Figure 5:
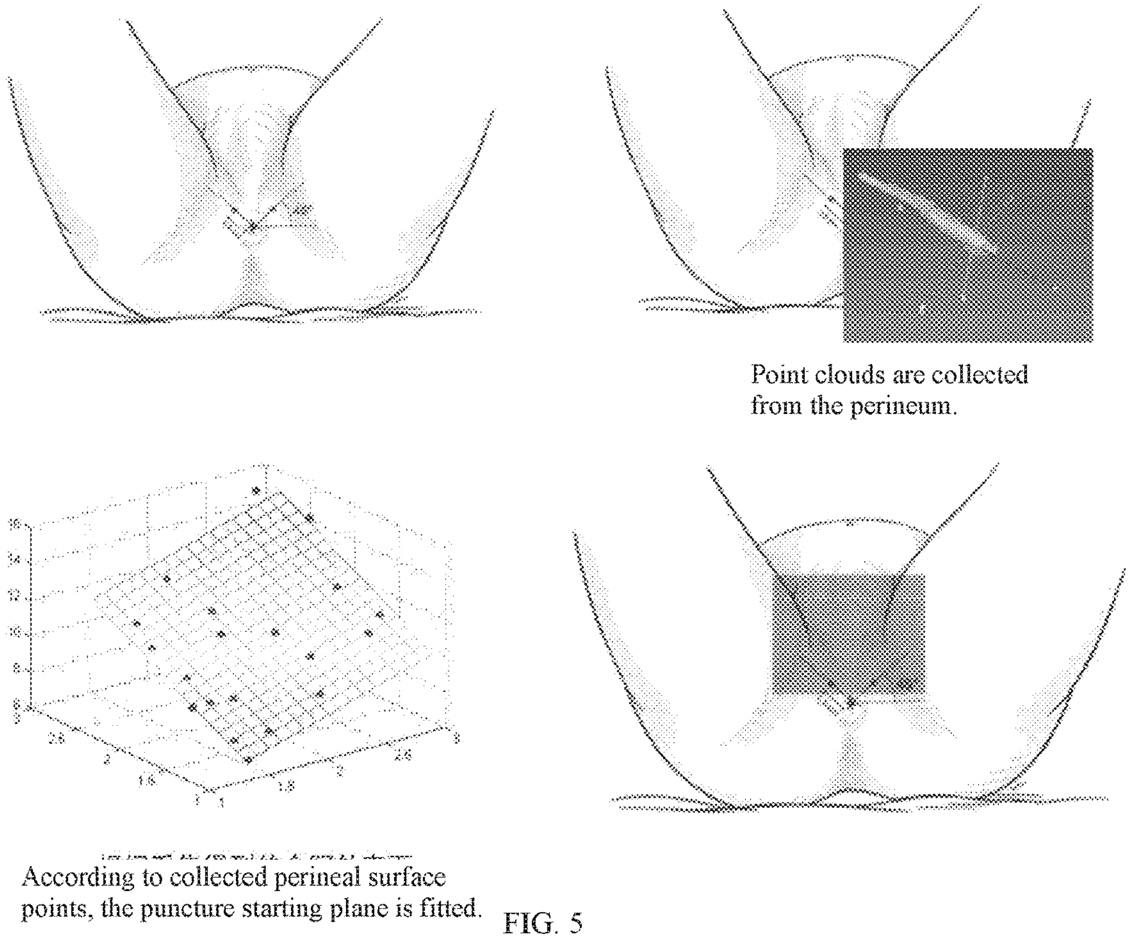
FIG. 5 is a schematic diagram showing the starting plane of the puncturing according to an embodiment of the present invention.

An intelligent anesthetization system for transperineal prostate puncturing based on the multimodal medical images which comprises:

Coordinate system definition module: Define electromagnetic emitter coordinate system CSe based on ultrasonic imaging plane formed by the electromagnetic field transmitter, define the nuclear magnetic imaging coordinate system CSm based on the nuclear magnetic device for taking MRI sequence images and define coordinate system CSs based on electromagnetic sensor which is fixed on the ultrasonic probe; obtain transformation matrix TMse of electromagnetic sensor at any position and posture in CSs based on position of electromagnetic sensor in the electromagnetic emitter coordinate system CSe. As shown in FIG. 4, it is explained that MRI is preoperative image, and probe position in US coordinate system needs to be calculated through registration to achieve effective surgical navigation.

The transformation matrix TMse is specifically:

$$TMse = \begin{bmatrix} R & T \\ 0 & 1 \end{bmatrix}$$

Wherein: R is a 3×3 matrix, T is a 3×1 vector, R and T represent the position and posture of electromagnetic sensor in the electromagnetic emitter coordinate system CSe.

Markup of MRI sequence images and 3D reconstruction module: Receive MRI sequence images of the human prostate, mark anesthetized area MRI-VMa and outer contour area of prostate MRI-VMp; reconstruct 3D anesthetized area and 3D outer contour area of prostate based on the position information of MRI sequence images;

Ultrasonic data extraction module: Receive ultrasonic data of the human prostate, extract image set covering base to apex of the prostate in ultrasonic data, and obtain outer contour area of prostate US-VMp in the electromagnetic emitter coordinate system CSe under ultrasonic images based on the spatial position information of each frame of ultrasonic image;

Registration module: Use ICP point cloud registration algorithm to register volume data about the outer contour area of prostate MRI-VMp in nuclear magnetic imaging coordinate system CSm as well as volume data about the outer contour area of prostate US-VMp in electromagnetic emitter coordinate system CSe under ultrasonic images and obtain spatial transformation matrix TMme between the two;

Anesthetic planning module: Receive the current ultrasonic images acquired by ultrasonic probe, obtain the anesthetized area EMTS-Vma mapped under electromagnetic emitter coordinate system based on the spatial transformation matrix TMme, and fuse it with current ultrasonic image to obtain the anesthetized area under ultrasonic images.

In this embodiment, images in preoperative nuclear magnetic imaging coordinate system and target area of anesthetization are transformed into real-time electromagnetic emitter coordinate system via multimodal medical image registration, thereby realizing comprehensive fusion of target area of anesthetization in nuclear magnetic resonance image and ultrasonic images which can be used for medical teaching or surgical guidance and can help to achieve precise positioning of anesthetized area for transperineal prostate biopsy.

Embodiment 2

Figure 1:
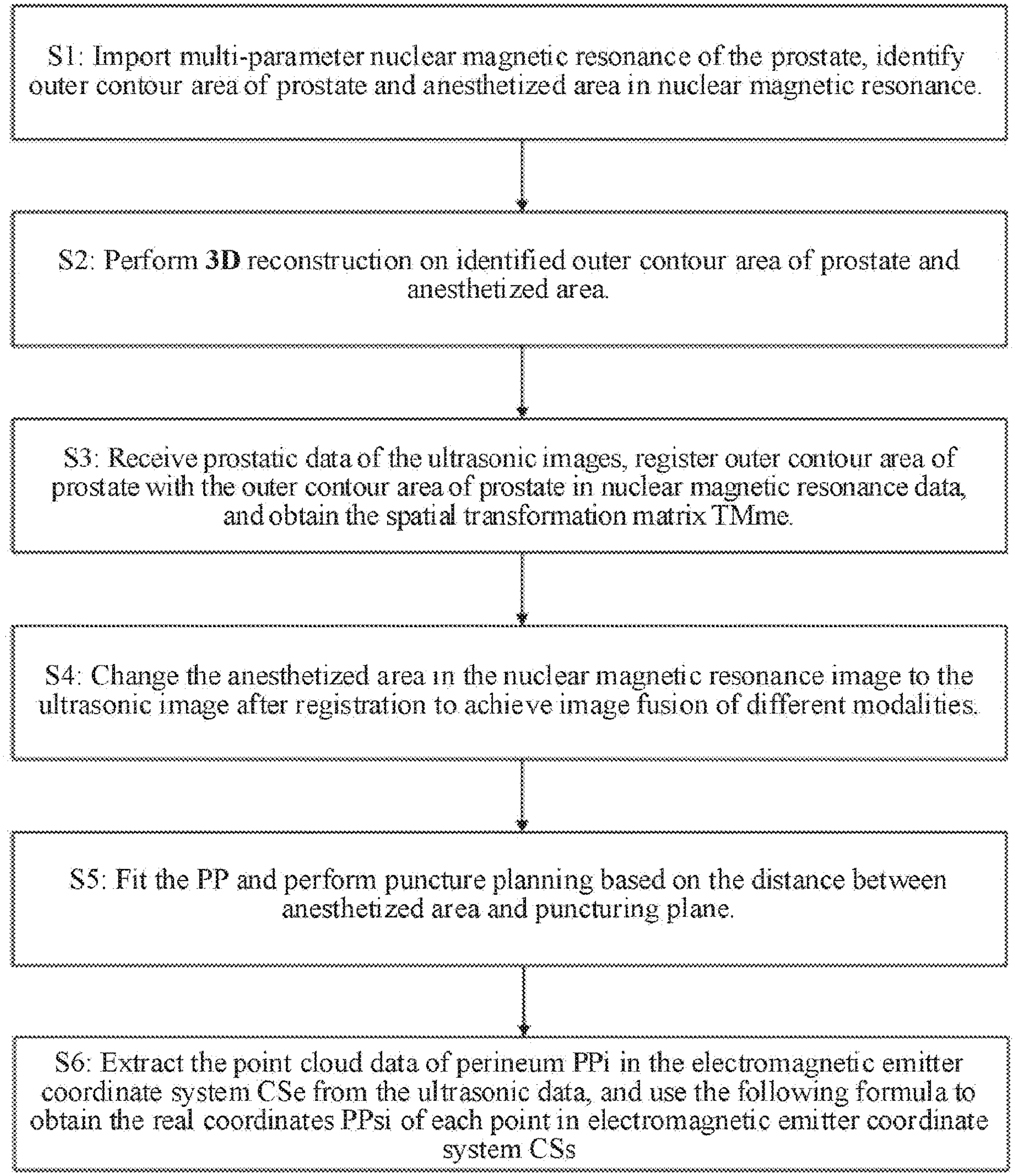
FIG. 1 is a flow chart of framework for implementing the system of the present invention.
Figure 2:
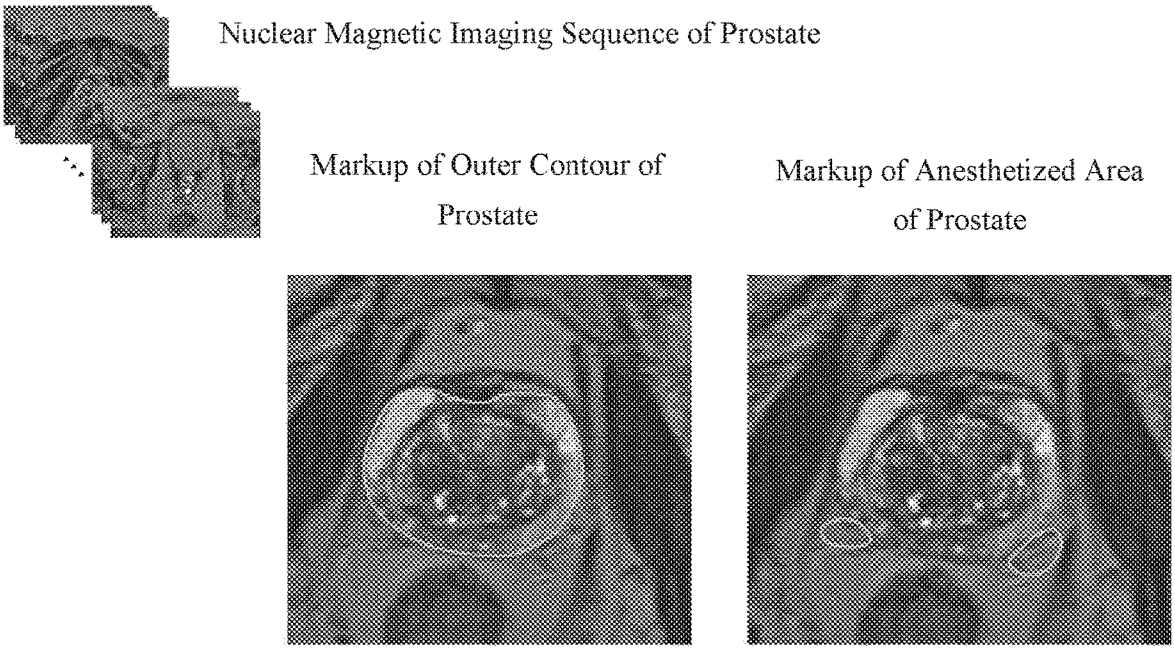
FIG. 2 is a schematic diagram showing prostate periphery and the markup of anesthetized area according to an embodiment of the present invention.
Figure 3:
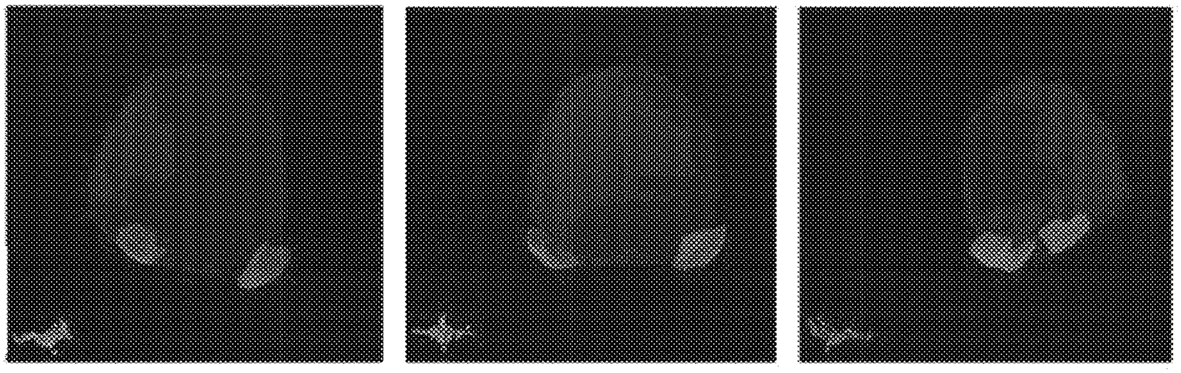
FIG. 3 is a schematic diagram showing the prostate periphery, anesthetized area and its 3D reconstruction according to an embodiment of the present invention.

In the present invention, steps of markup of MRI sequence images and 3D reconstruction module are specifically: Use the pre-trained deep learning model for the prostate segmentation to segment MRI sequence images and mark the segmented anesthetized area VMa and outer contour area of prostate VMp. As shown in FIG. 2, according to the imported nuclear magnetic resonance image, images containing peripheral area of prostate and the anesthetized area are marked to obtain peripheral contoured as well as anesthetized area. As shown in FIG. 3, after all the images in FIG. 2 are correctly marked, 3D reconstruction of corresponding MRI peripheral contoured area and anesthetized area can be completed, wherein the middle area is the prostate periphery and the areas on both sides are anesthetized area around the prostate.

Among them, deep learning model for prostate segmentation is specifically established as follows:

- Extract the cross-sectional and sagittal images of MRI sequence images of the prostate;
- Mark and segment anesthetized area and outer contour area of prostate on cross-sectional and sagittal images;
- Input marked and segmented MRI images of prostate as samples into the artificial neural network model for training to obtain the deep learning model for prostate segmentation.

In this embodiment, prostate is segmented and marked based on the deep learning model which effectively improves the accuracy of segmentation and recognition.

Embodiment 3

In present invention, acquisition of outer contour area of prostate US-VMp is specifically:

- Extract image set covering base to apex of the prostate in ultrasonic data, and the frame number is recorded as N;
- Extract images containing prostatic organ and segment the outer contour area of prostate to obtain outer contour area of prostate US-VMp in the ultrasonic images, and obtain coordinate PCe of each point within outer contour area in electromagnetic emitter coordinate system CSe using the following formula:

$$PCe_{(i,u,v)} = TMsei \times TMts \times (u, v, 0, 1);$$

Wherein i represents frame number, (u, v) represents pixel coordinates of contour point in ultrasonic 2D images, TMsei represents transformation matrix of electromagnetic sensor at any position in CSs corresponding to i-th frame image, and TMts represents transformation matrix of the relative positions between vertices of ultrasonic imaging plane and electromagnetic sensor.

Figure 6:
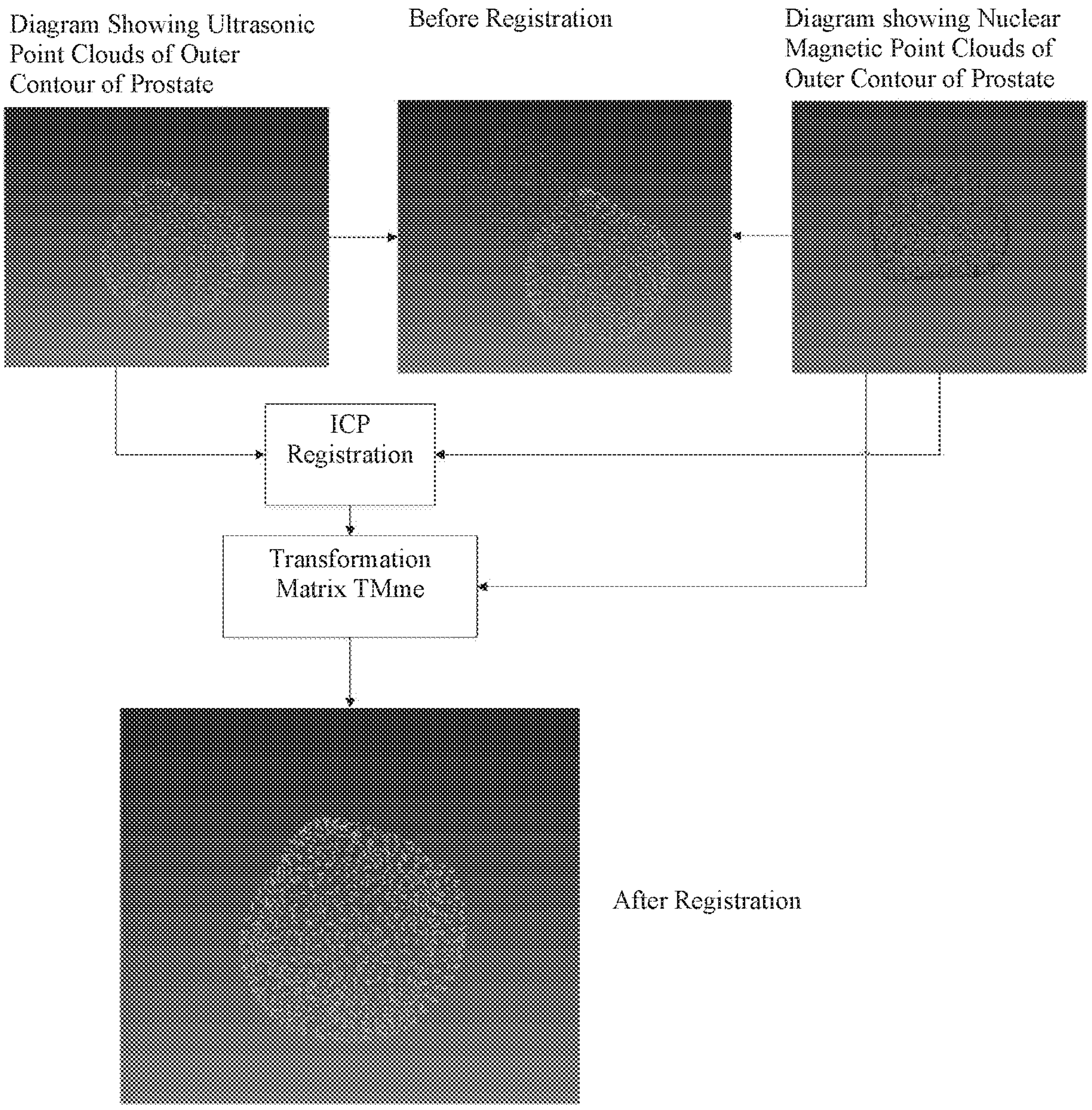
FIG. 6 is a schematic diagram showing ultrasonic images and point clouds registration of prostate periphery under nuclear magnetic resonance imaging according to an embodiment of the present invention.

In this embodiment, among the N frames of images collected, not only image containing prostatic organ is found but also outer contour area of prostate is segmented and outlined area as well as outer contour area of prostate in ultrasonic image is obtained. The coordinates of each point in the outer contour within electromagnetic emitter coordinate system CSe are obtained by formula transformation as shown in the first point cloud in FIG. 6 which represents position of each point in the ultrasonic outer contour area of prostate in CSe coordinate system.

Embodiment 4

In the present invention, registration module uses coordinates $PCe_{(i,u,v)}$ of each point in the outer contour area of prostate US-VMp within the ultrasonic image in electromagnetic emitter coordinate system CSe as first set of 3D point clouds and uses 3D point cloud corresponding to the 3D outer contour area of prostate MRI-VMp as the second set of 3D point clouds;

- Process two sets of the point clouds separately, including: triangulating and smoothing two sets of point clouds, restoring them into point clouds, downsampling to reduce the number of 3D point clouds, and obtaining two sets of downsampled 3D point clouds;
- Register processed 3D point clouds using ICP point cloud registration algorithm to obtain spatial transformation matrix TMme from the nuclear magnetic imaging coordinate system CSm to the electromagnetic emitter coordinate system CSe.

In this embodiment, the ICP algorithm is used to complete registration of two sets of point clouds, and transformation matrix TMme from nuclear magnetic imaging coordinate system to electromagnetic emitter coordinate system can be obtained. It can be seen that the prostate point cloud in the nuclear magnetic resonance is transformed by TMme to obtain the point cloud shown in schematic diagram FIG. 6 after registration which is basically consistent with position as well as orientation of point cloud corresponding to the ultrasound.

Embodiment 5

In the present invention, anesthetic planning module performs the following steps:

- Transform the anesthetized area MRI-VMa under nuclear magnetic imaging coordinate system CSm into electromagnetic emitter coordinate system under current ultrasonic image based on spatial transformation matrix TMme to obtain the mapped anesthetized area EMTS-Vma;
- Obtain a slice formed by tangency of plane position of current ultrasonic image and of volume data of anesthetized area EMTS-Vma to obtain the slice Sa with outline of the anesthetized area;
- Fuse and superimpose current ultrasonic image and slice Sa with outline of anesthetized area to obtain a fused image of current ultrasonic image and the anesthetized area which displays the anesthetized area under the ultrasonic images.

Figure 7:
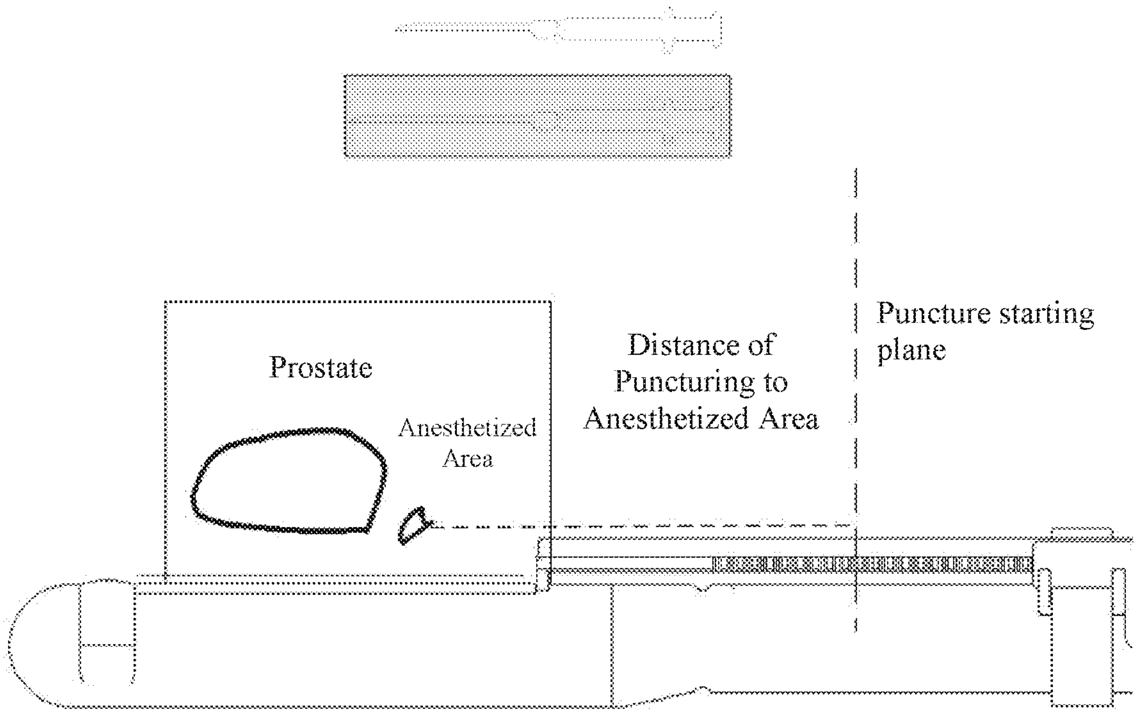
FIG. 7 is a schematic diagram showing navigation of the anesthetized area based on fusion according to an embodiment of the present invention.

In this embodiment, as shown in FIG. 7, the anesthetized area is also transformed into the coordinate system of the ultrasound based on transformation matrix, thereby completing the fusion of anesthetized area and ultrasonic 2D image. The anesthetized area marked in MRI is projected into the ultrasonic image, thereby achieving the fusion of ultrasonic image and MRI image. The fusion results can be used for medical teaching or surgical guidance to help to achieve the accurate positioning of the anesthetized area for transperineal prostate biopsy.

Embodiment 6

The system which includes a puncture planning module as well performs the following steps:

- Extract point cloud data of perineum in electromagnetic emitter coordinate system CSe from ultrasonic data, and obtain a series of coordinate points PPi(x, y, z, 1) on ultrasonic imaging plane wherein i represents serial number of coordinate points, x, y, z represent coordinate values of ultrasonic imaging plane respectively, and use the following formula to obtain real coordinates PPsi of each point in electromagnetic emitter coordinate system CSs;

$$PPsi = TMse \times TMts \times PPi$$

Wherein: TMts represents transformation matrix of relative positions between vertices of ultrasonic imaging plane and electromagnetic sensor;

Fit plane position of perineum PP as puncture starting plane by the SVD method based on discrete points according to real coordinates PPsi of each point. The normal vector of this plane is consistent with the direction of the ultrasonic probe entering the human body;

$$ax + by + cz + d = 0$$

Calculate the distance from center point of mapped anesthetized area EMTS-Vma under ultrasonic image to puncture starting plane PP using the following formula:

$$d = |ax_m + by_m + cz_m + d| / (a^2 + b^2 + c^2)$$

Wherein ($x_m$, $y_m$, $z_m$) is the center point of the anesthetized area in electromagnetic emitter coordinate system CSe of ultrasonic imaging plane, and a, b, c, d are plane parameters of PP.

Recommend anesthetic needle with suitable length based on distance from anesthetized area to puncture starting plane.

In this embodiment, as shown in FIG. 7, distance d from anesthetized area in ultrasonic coordinate system to fitted puncture starting plane PP is calculated, and the anesthetic needle with different lengths is recommended according to the different distances. FIG. 7 shows that when distance reaches a certain value, a longer anesthetic needle is recommended to achieve intelligent anesthetization program planning for transperineal puncturing biopsy of prostate. In this way, the anesthetization work can be carried out more smoothly and efficiently which plays effective role in promoting procedure in transperineal prostate biopsy.

The application method for system of the present invention is as follows:

Step 1 is to define electromagnetic emitter coordinate system CSe based on the ultrasonic imaging plane formed by the electromagnetic field transmitter, to define nuclear magnetic imaging coordinate system CSm based on nuclear magnetic device for taking MRI sequence images and to define coordinate system CSs based on electromagnetic sensor which is fixed on ultrasonic probe; to obtain transformation matrix TMse of the electromagnetic sensor at any position in CSs based on position and posture of electromagnetic sensor in electromagnetic emitter coordinate system CSe;

Step 2 is to receive MRI sequence images of human prostate, to use a pre-trained deep learning model for prostate segmentation to segment MRI sequence images and to mark segmented anesthetized area VMa and the outer contour area of prostate VMp; to reconstruct 3D anesthetized area as well as 3D outer contour area of prostate based on position information of MRI sequence images;

Step 3 is to extract image set covering base to apex of prostate in ultrasonic data, and frame number is recorded as N;

To extract the image containing prostatic organ and to segment the outer contour area of prostate to obtain outer contour area of prostate US-VMp in the ultrasonic image;

Step 4 is to use coordinates $PCe_{(i,u,v)}$ of each point in the outer contour area of prostate US-VMp within ultrasonic image in the electromagnetic emitter coordinate system CSe as the first set of 3D point clouds; to use 3D point clouds corresponding to 3D outer contour area of prostate MRI-VMp as the second set of 3D point clouds;

To process the two sets of point clouds separately;

To register processed 3D point clouds using ICP point cloud registration algorithm to obtain spatial transformation matrix TMme from the nuclear magnetic imaging coordinate system CSm to the electromagnetic emitter coordinate system CSe;

Step 5 is to receive current ultrasonic image acquired by ultrasonic probe, to transform the anesthetized area MRI-VMa in nuclear magnetic imaging coordinate system CSm into the electromagnetic emitter coordinate system under the current ultrasonic image based on spatial transformation matrix TMme and to obtain the mapped anesthetized area EMTS-Vma;

To obtain a slice formed by tangency of plane position of current ultrasonic image and of volume data of anesthetized area EMTS-Vma to obtain the slice Sa with outline of anesthetized area;

To fuse and superimpose the current ultrasonic image and the slice Sa with the outline of anesthetized area to obtain a fused image of the current ultrasonic image and the anesthetized area which displays the anesthetized area under the ultrasonic image;

Step 6 is to extract the point cloud data of perineum PPi in the electromagnetic emitter coordinate system CSe from the ultrasonic data, and to use the following formula to obtain the real coordinates PPsi of each point in electromagnetic emitter coordinate system CSs;

$$PPsi = TMse \times TMts \times PPi$$

Wherein: TMts represents transformation matrix of relative positions between vertices of ultrasonic imaging plane and electromagnetic sensor;

To fit plane position PP of perineum as puncture starting plane by the SVD method based on discrete points according to the real coordinates PPsi of each point;

To calculate the distance d from center point of anesthetized area EMTS-Vma mapped under current ultrasonic image to puncture starting plane PP, and recommends anesthetic needle with suitable length based on distance from anesthetized area to puncture starting plane.

When system of the present invention is applied, it realizes comprehensive fusion of the target area of anesthetization in MRI and ultrasonic image which can be used for medical teaching or surgical guidance and can help to achieve the precise positioning of anesthetized area for the transperineal prostate biopsy. It also realizes intelligent recommendation of model of the anesthetic needle by calculating and analyzing distance between target area and starting position of needle insertion, making the working progress of the anesthetization more smoothly as well as efficiently and playing effective role in promoting procedure in transperineal prostate biopsy.

The embodiments of present invention have been described above, and above description is exemplary, not exhaustive, and is not limited to the disclosed embodiments. Without departing from scope and spirit of the embodiments described, many of the modifications as well as changes are obvious to the average technician in the field of technology.

What is claimed is:

1. An intelligent anesthetization system for a transperineal prostate puncturing based on multimodal medical images, comprising:

an electromagnetic field transmitter; and ultrasonic probe configured to acquire ultrasonic data and a current ultrasonic image; an electromagnetic sensor fixed on the ultrasonic probe; and a nuclear magnetic device configured to obtain magnetic resonance image (MRI) sequence images, wherein coordinate system definitions comprises: define an electromagnetic emitter coordinate system CSe based on the ultrasonic imaging plane formed by the electromagnetic field transmitter, define a nuclear magnetic resonance imaging coordinate system CSm based on the nuclear magnetic device for taking the magnetic resonance image (MRI) sequence images and define a coordinate system CSs based on the electromagnetic sensor and obtain a transformation matrix $$TMse = \begin{bmatrix} R & T \\ 0 & 1 \end{bmatrix}$$

of the electromagnetic sensor at any position in CSs based on a position and posture of the electromagnetic sensor in the electromagnetic emitter coordinate system CSe, wherein R is a 3×3 matrix and T is a 3×1 vector;

wherein MRI sequence image markup and 3D reconstruction comprises: receive MRI sequence images of human prostate, mark anesthetized area MRI-VMa and outer contour area of the prostate MRI-VMp; reconstruct 3D anesthetized area and 3D outer contour area of prostate based on position information of the MRI sequence images;

wherein ultrasonic data extraction comprises: receive ultrasonic data of the human prostate, extract an image set covering base to apex of the prostate in the ultrasonic data, and obtain the outer contour area of prostate US-VMp in the electromagnetic emitter coordinate system CSe under ultrasonic images based on spatial position information of each frame of ultrasonic image, and obtain the coordinate PCe(i,u,v)=TMsei×TMts×(u, v,0,1) of each point within the outer contour area in the electromagnetic emitter coordinate system CSe, wherein i represents a frame number, (u, v) represents pixel coordinates of contour point in ultrasonic 2D images, TMsei represents a transformation matrix of the electromagnetic sensor at any position in CSs corresponding to an i-th frame image, and TMts represents a transformation matrix of relative positions between vertices of the ultrasonic imaging plane and the electromagnetic sensor;

wherein registration comprises: use an iterative closest point (ICP) point cloud registration algorithm to register volume data about the outer contour area of prostate MRI-VMp in the nuclear magnetic resonance imaging coordinate system CSm as well as volume data about the outer contour area of prostate US-VMp in the electromagnetic emitter coordinate system CSe under the ultrasonic image and obtain a spatial transformation matrix TMme between the nuclear magnetic resonance imaging coordinate system CSm and the electromagnetic emitter coordinate system CSe;

anesthetic planning comprises: receive the current ultrasonic image acquired by the ultrasonic probe, transform the anesthetized area MRI-VMa in the nuclear magnetic resonance imaging coordinate system CSm into the electromagnetic emitter coordinate system under the current ultrasonic image based on the spatial transformation matrix TMme to obtain the mapped anesthetized area EMTS-Vma, obtain a slice formed by tangency of a plane position of the current ultrasonic image and of volume data of the anesthetized area EMTS-Vma to obtain slice Sa with an outline of the anesthetized area, and fuse and superimpose the current ultrasonic image and the slice Sa with the outline of the anesthetized area to obtain the anesthetized area under the ultrasonic images.

2. The intelligent anesthetization system for the transperineal prostate puncturing based on the multimodal medical images according to claim 1, wherein the MRI sequence image markup uses a pre-trained deep learning model for prostate segmentation to segment the MRI sequence images to obtain a segmented anesthetized area VMa and an outer contour area of prostate VMp, and marks the segmented anesthetized area VMa and the outer contour area of prostate VMp.

3. The intelligent anesthetization system for the transperineal prostate puncturing based on the multimodal medical images according to claim 2, wherein the pre-trained deep learning model for prostate segmentation is established as follows:

extract cross-sectional and sagittal images of MRI sequence images of the prostate;

mark and segments the anesthetized area and the outer contour area of prostate on the cross-sectional and sagittal images; and input marked and segmented MRI images of the prostate as samples into an artificial neural network model for training to obtain the pre-trained deep learning model for prostate segmentation.

4. The intelligent anesthetization system for the transperineal prostate puncturing based on the multimodal medical images according to claim 1, wherein obtaining the outer contour area of prostate US-VMp comprises:

extract the image set covering base to apex of the prostate in the ultrasonic data, and a number of frames is recorded as N; and extract images containing prostatic organ and segment the outer contour area of prostate to obtain the outer contour area of the prostate US-VMp in the ultrasonic images, and obtain the coordinate PCe of each point within the outer contour area in the electromagnetic emitter coordinate system CSe using the following formula:

$$PCe_{(i,u,v)} = TMsei \times TMts \times (u, v, 0, 1);$$

wherein i represents a frame number, (u, v) represents pixel coordinates of contour point in ultrasonic 2D images, TMsei represents a transformation matrix of the electromagnetic sensor at any position in CSs corresponding to an i-th frame image, and TMts represents a transformation matrix of relative positions between vertices of the ultrasonic imaging plane and the electromagnetic sensor.

5. The intelligent anesthetization system for the transperineal prostate puncturing based on the multimodal medical images according to claim 1, wherein registration comprises:

use coordinates $PCe_{(i,u,v)}$ of each point in the outer contour area of prostate US-VMp within the ultrasonic image in the electromagnetic emitter coordinate system CSe as a first set of 3D point clouds and use 3D point cloud corresponding to the 3D outer contour area of prostate MRI-VMp as a second set of 3D point clouds;

process the first set of 3D point clouds and the second set of 3D point clouds separately to obtain processed 3D point clouds; and register the processed 3D point clouds using the ICP point cloud registration algorithm to obtain the spatial transformation matrix TMme from the nuclear magnetic resonance imaging coordinate system CSm to the electromagnetic emitter coordinate system CSe.

6. The intelligent anesthetization system for the transperineal prostate puncturing based on the multimodal medical images according to claim 1, wherein anesthetic planning comprises the following steps:

transform the anesthetized area MRI-VMa in the nuclear magnetic resonance imaging coordinate system CSm into the electromagnetic emitter coordinate system under current ultrasonic images based on the spatial transformation matrix TMme to obtain the mapped anesthetized area EMTS-Vma;

obtain a slice formed by tangency of a plane position of the current ultrasonic image and of volume data of the anesthetized area EMTS-Vma to obtain slice Sa with an outline of the anesthetized area; and fuse and superimpose the current ultrasonic image and the slice Sa with the outline of the anesthetized area to obtain a fused image of the current ultrasonic image and the anesthetized area, wherein the fused image displays the anesthetized area under the ultrasonic images.

7. The intelligent anesthetization system for the transperineal prostate puncturing based on the multimodal medical images according to claim 1, further configured to perform the following steps:

extract point cloud data of perineum in the electromagnetic emitter coordinate system CSe from the ultrasonic data and fits a plane position of perineum PP as an initial plane position of the needle into human body, which its normal vector of this plane is consistent with a direction of the ultrasonic probe entering the human body; and calculate a distance from a center point of the mapped anesthetized area EMTS-Vma under the ultrasonic image to a puncture starting plane PP, and recommend an anesthetic needle with a suitable length based on the distance from the anesthetized area to the puncture starting plane.

8. The intelligent anesthetization system for the transperineal prostate puncturing based on the multimodal medical images according to claim 7, wherein fitting of the plane position PP of perineum comprises:

extract an ultrasonic data sequence of perineum, and obtain a series of coordinate points PPi(x, y, z, 1) on the ultrasonic imaging plane, wherein i represents a serial number of coordinate points, x, y, z represent coordinate values of the ultrasonic imaging plane respectively, and use the following formula to obtain real coordinates PPsi of each point in the electromagnetic emitter coordinate system CSs;

$$PPsi = TMse \times TMts \times PPi$$

wherein: TMts represents a transformation matrix of relative positions between vertices of the ultrasonic imaging plane and the electromagnetic sensor; and fit the plane position PP of perineum as the puncture starting plane by a singular value decomposition (SVD) method based on discrete points according to the real coordinates PPsi of each point;

$$ax + by + cz + d = 0.$$

9. The intelligent anesthetization system for the transperineal prostate puncturing based on the multimodal medical images according to claim 8, wherein the distance from the center point of the mapped anesthetized area EMTS-Vma to the puncture starting plane PP is calculated using the following formula:

$$d = |ax_m + by_m + cz_m + d|/\left(a^2 + b^2 + c^2\right)$$

wherein $(x_m, y_m, z_m)$ is the center point of the anesthetized area in the electromagnetic emitter coordinate system CSe of the ultrasonic imaging plane, and a, b, c, d are plane parameters of PP.

* * * * *